US010377756B2

(12) United States Patent
Ametamey et al.

(10) Patent No.: US 10,377,756 B2
(45) Date of Patent: Aug. 13, 2019

(54) $^{18}$F-LABELLED FOLATES

(71) Applicant: MERCK & CIE, Schaffhausen (CH)

(72) Inventors: Simon Mensah Ametamey, Zurich (CH); Rudolf Moser, Schaffhausen (CH); Tobias Ludwig Ross, Zurich (CH); Phoebe Lam, Zurich (CH); Viola Groehn, Dachsen (CH)

(73) Assignee: MERCK & CIE, Schaffhausen (CH)

( * ) Notice: Subject to any disclaimer, the term of this patent is extended or adjusted under 35 U.S.C. 154(b) by 271 days.

(21) Appl. No.: 14/797,640

(22) Filed: Jul. 13, 2015

(65) Prior Publication Data
US 2015/0315189 A1 Nov. 5, 2015

Related U.S. Application Data

(62) Division of application No. 12/595,405, filed as application No. PCT/EP2008/054404 on Apr. 11, 2008.

(30) Foreign Application Priority Data

Apr. 11, 2007 (EP) ..................... 07105976

(51) Int. Cl.
A61K 51/00 (2006.01)
A61M 36/14 (2006.01)
C07D 475/04 (2006.01)
A61K 51/04 (2006.01)
C07B 59/00 (2006.01)

(52) U.S. Cl.
CPC ........ C07D 475/04 (2013.01); A61K 51/0459 (2013.01); A61K 51/0497 (2013.01); C07B 59/002 (2013.01)

(58) Field of Classification Search
CPC .............. C07D 475/04; A61K 51/0459; A61K 51/0497; C07B 59/002
USPC ........................................................ 424/1.89
See application file for complete search history.

(56) References Cited

U.S. PATENT DOCUMENTS

| 3,989,812 | A |  | 11/1976 | Barrett et al. |
| 4,115,065 | A |  | 9/1978 | Bayly et al. |
| 4,202,976 | A |  | 5/1980 | Bayly et al. |
| 4,276,280 | A |  | 6/1981 | Akerkar et al. |
| 4,298,735 | A |  | 11/1981 | Farina et al. |
| 4,314,988 | A |  | 2/1982 | Farina et al. |
| 4,326,060 | A |  | 4/1982 | Farina et al. |
| 4,337,339 | A |  | 6/1982 | Farina et al. |
| 4,584,375 | A |  | 4/1986 | Coward |
| 4,628,090 | A |  | 12/1986 | Coward |
| 5,066,828 | A |  | 11/1991 | Bey et al. |
| 5,286,726 | A |  | 2/1994 | Bey et al. |
| 6,093,382 | A | * | 7/2000 | Wedeking ............ A61K 49/085 424/1.11 |
| 8,586,595 | B2 | * | 11/2013 | Low .................. A61K 51/0497 514/262.1 |
| 2005/0227985 | A9 | * | 10/2005 | Green et al. .................. 514/243 |

FOREIGN PATENT DOCUMENTS

| EP | 0451835 A1 | 10/1991 |
| EP | 0451836 A2 | 10/1991 |
| GB | 1501119 A | 2/1978 |
| JP | 61044890 A | 3/1986 |
| JP | 61044890 W | 3/1986 |
| WO | 1999020626 | 4/1999 |
| WO | 2002085908 | 10/2002 |
| WO | 2003092742 | 11/2003 |
| WO | WO 2005097713 A1 * | 10/2005 |
| WO | 2006071754 | 7/2006 |
| WO | 2006071754 A2 | 7/2006 |
| WO | 2006101845 | 9/2006 |
| WO | 2006116629 | 11/2006 |
| WO | 2007006041 | 1/2007 |
| WO | 2007022493 | 2/2007 |
| WO | 2007022494 | 2/2007 |
| WO | 2007038346 | 4/2007 |
| WO | 2007139815 | 12/2007 |
| WO | 2008054404 | 8/2008 |
| WO | 2008098112 A2 | 8/2008 |

OTHER PUBLICATIONS

Bettio et al. J Nucl. Med. 2006; 47:1153-1160.*
Chi et al. J. Org. Chem. 1987, 52, 658-664.*
Ferrieri et al. Handbook Radioparm: Radiochem. Appl. 2003, 229-282.*
Tewson, T.J., "Synthesis of [18F] fluoroetanidazole: a potential new tracer for imaging hypoxia", Nuclear Medicine and Biology, 1997, vol. 24, No. 8, p. 755-760.
Zhang, M.R. et al, "How to increase the reactivity of [18F]fluoroethyl bromide: [18F]fluoroethylation of amine, phenol and amide functional groups with [18F]FEtBr, [18F]FEtBr/NaI and [18F]FEtOTf", Journal of Labelled Compound and Radiopharmaceuticals, vol. 46, pp. 587-598 (2003).
Gilissen, C. et al, "Synthesis of N-(2-[18F] fluoroethyl)-N'-methylthiourea: a hydrogen peroxide scavenger", Journal of Labelled Compounds & Radiopharmaceuticals, 1998, vol. 41, No. 6, p. 491-502.
Barthel, H. et al, "In vivo evaluation of [18F] fluoroetanidazole as a new marker for imaging tumour hypoxia with positron emission tomography", British Journal of Cancer, 2004, vol. 90, No. 11, p. 2232-2242.

(Continued)

Primary Examiner — Michael G. Hartley
Assistant Examiner — Sean R Donohue
(74) Attorney, Agent, or Firm — Millen, White, Zelano & Branigan, P.C.

(57) ABSTRACT

The present invention is directed towards a new method of synthesis of $^{18}$F-folate radiopharmaceuticals, wherein fluorine-18 is attached to a pteroate (or folate) or derivative thereof, through direct radiolabeling with $^{18}$[F]fluoride, as well as $^{18}$F-folate radiopharmaceuticals obtained by such method of synthesis and their use in diagnosis and monitoring of cancer therapy and therapy of inflammatory and autoimmune diseases.

14 Claims, No Drawings

(56) References Cited

OTHER PUBLICATIONS

Chi et al., JOC, 1987, vol. 52, pp. 658-664.
McGuire et al., Biochem., Pharmacol. 1996, vol. 52, pp. 1295-1303.
Betrio, A. et al., "Synthesis and Preclinical Evaluation of a Folic Acid Derivative Labeled with 18F for PET Imaging of Folate Receptor-Positive Tumors,", Journal of Nuclear Medicine), 2006, vol. 47, pp. 1153-1160.
Marik, J. et al., "Click for PET: Rapid Preparation of [18F]-fluoropeptides using Cu(I) Catalysed 1,3-Dipolar Cycloaddition," (Tetrahedron Letters), 2006, vol. 47, pp. 6681-6684.
Paul A. Jerabek et al., "Synthesis and Biodistribution of 18F-Labeled Fluoronitroimidazoles: Potential in vivo Marker of Hypoxic Tissue", Appl. Radiat. Isot., vol. 37, No. 7, pp. 599-605, 1986.
Dale O. Kiesewetter et al., "Syntheses and D2 Receptor Affinities of Derivatives of Spiperone Containing Aliphatic Halogens", Appl. Radial Isot., vol. 37, No. 12, pp. 1181-1188, 1986.

* cited by examiner

[18]F-LABELLED FOLATES

FIELD OF INVENTION

The present invention is directed towards a new method of synthesis of $^{18}$F-labeled pteroate or folate radiopharmaceuticals, wherein fluorine-18 is attached to a pteroate (or folate) or derivative thereof, through direct radiolabeling with [18][F]fluoride, as well as $^{18}$F-folate radiopharmaceuticals obtained by such method of synthesis and their use in diagnosis and monitoring of cancer therapy and therapy of inflammatory and autoimmune disease.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or photons or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific structures and in particular structures that are present in case of tumors (i.e. cancer) or inflammatory and autoimmune diseases, such as receptors, antigens, haptens and the like which can be specifically targeted by the respective biological vehicles.

The folate receptor (FR) has been identified as one of these structures. In normal tissues and organs FR-expression is highly restricted to only a few organs (e.g. kidney, lungs, choroids plexus, and placenta). Yet, the FR-alpha is frequently overexpressed on a wide variety of specific cell types, such as epithelial tumours (e.g. ovarian, cervical, endometrial, breast, colorectal, kidney, lung, nasopharyngeal), and the FR-beta is frequently overexpressed in leukaemia cells (approx. 70% of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition it has recently been discovered that activated (but not resting) synovial macrophages in patients diagnosed with rheumatoid arthritis possess a functionally active FR-beta (Nakashima-Matsushita et al, Arthritis & Rheumatism, 1999, 42(8): 1609-16). Therefore activated macrophages can be selectively targeted with folate conjugates in arthritic joints, a capability that opens possibilities for the diagnosis and treatment of rheumatoid arthritis (Paulos et al, Adv. Drug Deliv. Rev. 2004; 56:1205-17).

Various folic acid derivatives and conjugates are known and have been (pre)clinically evaluated. In particular, folate radiopharmaceuticals have increasingly gained importance in the field of nuclear medicine and can be very useful for an improved diagnosis and evaluation of the effectiveness of therapy of cancer and inflammatory and autoimmune diseases, such as assessment and/or prediction of a treatment response and consequently improvement of radiation dosimetry. A typical visualization technique which is suitable for radioimaging is PET. PET uses isotopes with short half lives, which are either covalently linked to its carrier or via a chelating moiety. Suitable isotopes include for example [11]C (ca. 20 min), [13]N (ca. 10 min), [15]O (ca. 2 min), and [18]F (ca. 110 min) as covalently bound nuclides and for example [68]Ga (ca. 68 min) which is usually linked by a chelating system.

Clearly, a folate radiopharmaceutical having a covalently linked isotope would be of great interest. In particular a $^{18}$F-labeled folate radiopharmaceutical would be most suitable for PET Imaging because of its excellent imaging characteristics which would fulfil all of the above considerations. Compared with other suitable radionuclides ($^{11}$C, $^{13}$N, $^{15}$O), $^{18}$F is very useful because of its long half-life of approximately 110 minutes and because it decays be emitting positrons having the lowest positron energy, which allows for the sharpest images with a high-resolution PET. Furthermore, the longer half-life of $^{18}$F also allows for syntheses that are more complex and satellite distribution to PET centers with no radiochemistry facilities.

Yet, the structure of folic acid does not lend itself to direct radiolabeling with [18]F. Thus, to date, mainly chelate-based folate radiopharmaceuticals have been synthesized and successfully evaluated as diagnostic agents for imaging folate receptor-positive tumors. The most widely studied derivatives were labeled either with $^{111}$In and $^{99m}$Tc for SPECT (Siegel et al., J. Nucl. Med. 2003, 44:700; Müller et al., J. Organomet. Chem. 2004, 689:4712) or with $^{68}$Ga for PET (Mathias et al., Nucl. Med. Biol. 2003, 30(7):725). In contrast, only very few folic acid derivatives have been reported in the literature which have been labelled with [18]F (Bettio et al., J. Nucl. Med., 2006, 47(7), 1153; WO 2006/071754). Typically, an intermediate of choice was radiofluorinated to obtain an $^{18}$F-labelling intermediate, which is subsequently activated and purified in order to be subjected to coupling to a functional group within folic acid, such as the carboxylic acid group within the glutamate part of folic acid.

Clearly, such a multi-step radiosynthesis is time-consuming and in fact gave typically only low radiochemical yields of less than 5% (Bettio et al., J. Nucl. Med., 2006, 47(7), 1153).

Thus, there is still a great need for an efficient and versatile approach for preparing directly radiolabeled $^{18}$F-folates or derivatives thereof, which addresses one or more of the above discussed drawbacks.

Applicants have now found an efficient and versatile method of synthesis of new $^{18}$F-labeled folate radiopharmaceuticals overcoming the drawbacks of conventional labelling methods, wherein fluorine-18 is attached to a folic acid or derivative thereof through direct radiolabeling with [18][F] fluoride.

Thus the present method is a time-saving and convenient direct $^{18}$F-labelling method, wherein no prosthetic groups are necessary and suitable precursors which carry only amide bounded activated groups as moieties for direct $^{18}$F-labelling are easy accessible.

In addition the present method allows regioselective preparation and labelling of the α- or γ-isomer with no need for separation, which is known to be difficult and time-consuming.

SUMMARY OF THE INVENTION

Thus, the present invention is in a first aspect directed to a new method of synthesis of $^{18}$F-labeled pteroate or folate radiopharmaceuticals (hereinafter also called method of the invention), wherein fluorine-18 is attached to a pteroate (or folate) or derivative thereof through direct radiolabeling with [18][F]fluoride.

In one specific embodiment, there is provided a method of synthesis of an $^{18}$F-labeled compound of general formula I

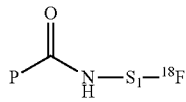

I wherein P is a pteroate and $S_1$ is a spacer,
comprising the steps of (a) providing a precursor of formula II,

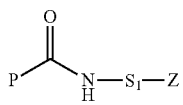

II wherein Z is a leaving group, and P and $S_1$ are defined as hereinabove, and (b) subjecting said precursor to direct radiolabeling with $^{18}$[F]fluoride to obtain a compound of formula I.

More specifically the present invention is directed towards a method of synthesis of an $^{18}$F-labeled compound of general formula I having the formula III

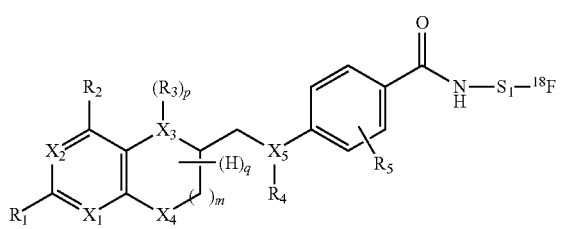

III wherein
$X_1$ to $X_5$ are independently of each other C or N,
$R_1$, $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
$R_5$ is H, CN, Hal, $NO_2$, C1-C12 alkyl, C1-C12 alkoxy, C1-C12 alkanoyl, C2-C12 alkenyl, C2-C12 alkynyl, (C1-C12 alkoxy)carbonyl, (C1-C12 alkylamino) carbonyl,
$S_1$ is a straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof, m is 0 or 1,
p is 0, 1 or 2, and
q has a value of 1 to 7,
comprising the steps of (a) providing a precursor of formula IV,

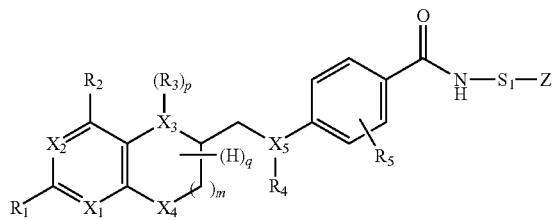

IV wherein Z is a leaving group, and $X_1$ to $X_5$, $R_1$ to $R_5$, $S_1$, p, and q are defined as hereinabove, and (b) subjecting said precursor to direct radiolabeling with $^{18}$[F]fluoride.

In a preferred embodiment, $^{18}$[F]fluoride in step (b) is activated by phase transfer catalysts such as tetrabutylamonium carbonate or aminopolyethers (e.g. Kryptofix© 2.2.2) in combination with potassium carbonate or oxalate.

Preferably, Z is a leaving group such as Hal, $NO_2$, diazonium salts, sulfonate esters, including mesylate $CH_3SO_2O$—, tosylate $CH_3C_6H_4SO_2O$—, pentafluorobenzoate, triflate$CF_3SO_2O$—, iodonium salts —$I^+R'''_2$, dialkyl/aryl silanes —$SiOHR'''_2$, and silanols —$SiHR'''_2$, wherein R''' is independently a straight-chain or branched $C_{(1-24)}$ alkyl group or an optionally substituted carbocyclic and heterocyclic group comprising five-, six- or ten-membered ring systems and the like.

Preferably, $S_1$ is a straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof.

In a further specific embodiment the present invention contemplates a method of synthesis wherein the obtained compound of general formula I has the formula V

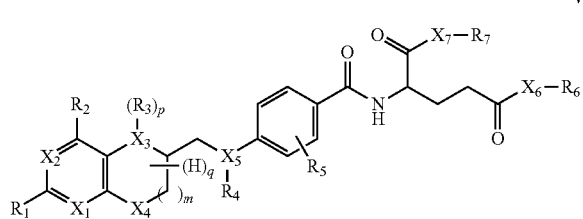

V wherein $X_6$, $X_7$ are independently of each other N or O, $R_6$, $R_7$ are independently of each other a group $R_5$ or a group $-S_2-^{18}F$, wherein $S_2$ is straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof, with the proviso that one of $R_6$ and $R_7$ is a group $-S_2-^{18}F$, and $X_1$ to $X_5$, $R_1$ to $R_5$, m, p and q, are as defined hereinabove.

In a further aspect the present invention is directed to new $^{18}F$-folate radiopharmaceuticals (hereinafter also called compounds of the invention), such as compounds of formulae I through V, obtained by the new method of direct radiofluorination of the invention, as well as pharmaceutical compositions and uses thereof, in particular uses in diagnosis and monitoring of cancer therapy and therapy of inflammatory and autoimmune diseases in vitro or in vivo.

In a specific embodiment, the present invention is directed towards uses of the compounds of the invention for diagnostic imaging of a cell or population of cells expressing a folate-receptor.

More specifically the present invention includes methods for diagnostic imaging of a cell or population of cells expressing a folate-receptor, which includes for example methods for in vitro detection of a cell expressing the folate receptor, for example a tumor cell, in a tissue sample. Such methods may also be performed in vivo.

Thus, in a further embodiment the present invention is directed towards uses of the compounds of the invention for convenient and effective administration to a subject in need for diagnostic imaging and/or monitoring of cancer therapy and therapy of inflammatory and autoimmune diseases. The subject of the methods of the present invention is preferably a mammal, such as an animal or a human, preferably a human.

Such methods may be performed in combination with any other methods of diagnosis or therapy of cancer and inflammatory and autoimmune diseases including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

Other features and advantages of the invention will be apparent from the following detailed description thereof and from the claims.

DETAILED DESCRIPTION OF THE INVENTION

The present invention is in a first aspect directed to a new method of synthesis of $^{18}F$-labeled pteroate or folate radiopharmaceuticals (hereinafter also called method of the invention), wherein fluorine-18 is attached through direct radiolabeling with $^{18}[F]$fluoride (hereinafter also abbreviated by "$^{18}F$").

In one specific embodiment, there is provided a method of synthesis of an $^{18}F$-labeled compound of general formula I

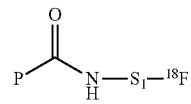

wherein P is a pteroate and $S_1$ is a spacer, comprising the steps of (a) providing a precursor of formula II,

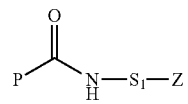

wherein Z is a leaving group, and P and $S_1$ are defined as hereinabove, and (b) subjecting said precursor to direct radiolabeling with $^{18}F$ to obtain a compound of formula I.

The term "pteroate" as used herein, comprises compounds based on a condensed pyrimidine heterocycle, which is linked to an aminobenzoyl moiety, which is then further derivatized in the paraposition with a covalently linked $S_1$-group as defined hereinafter. As used herein a "condensed pyrimidine heterocycle" includes a pyrimidine fused with a further 5- or 6-membered heterocycle, such as a pteridine or a pyrrolopyrimidine bicycle.

In a specific embodiment the term "pteroate" also includes folates, which as used herein are compounds based on a folate skeleton (i.e. based on pteroyl-glutamic acid or N-[4(pteridin-6-ylmethylamino)benzoyl]-glutamic acid), and derivatives thereof. These include optionally substituted folic acid, folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs.

More specifically the present invention is directed towards a method of synthesis depicted in Scheme 1, wherein a precursor IV, having a leaving group Z is directly radiolabeled with $^{18}F$ to obtain a compound of general formula I having formula III Scheme 1. Synthesis scheme

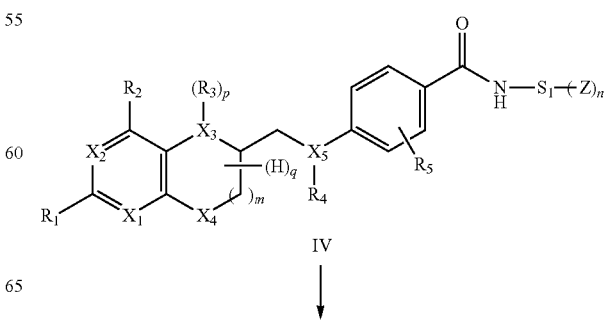

IV

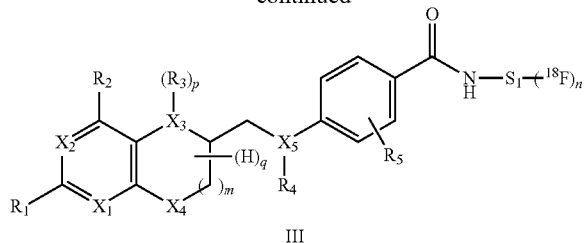

III

It was found that a pteroic (or folic) acid moiety of general formulae I or IV, respectively, may be $^{18}$F-radiolabeled easily and efficiently in a direct manner and thus with no need for synthesis and purification of an intermediate $^{18}$F-labelling agent.

Preferably, the direct radiolabeling of precursor IV is performed with $^{18}$F activated by phase transfer catalysts such as tetrabutylamonium carbonate or aminopolyethers (e.g. Kryptofix© 2.2.2) in combination with potassium carbonate or oxalate. In a specific embodiment, $^{18}$F is activated with Kryptofix, in a polar aprotic solvent selected from acetonitrile, acetone, 1,4-dioxane, tetrahydrofuran (THF), N-methylpyrrolidinone (NMP), di-methoxyethane (DME), dimethylacetamide (DMA), N,N-dimethylformamide (DMF), dimethytsulfoxide (DMSO) and hexa-methylphosphoramide (HMPA) and mixtures thereof.

The leaving group Z may be any common leaving group known in the art and includes for example Hal, $NO_2$, diazonium salts, sulfonate esters, including mesylate $CH_3SO_2O$—, tosylate $CH_3C_6H_4SO_2O$—, pentafluorobenzoate, triflate$CF_3SO_2O$—, iodonium salts —I$^+$R'''$_2$, dialkyl/-aryl silanes —SiOHR'''$_2$, and silanols —SiHR'''$_2$, wherein R''' is independently a straight-chain or branched $C_{(1-24)}$ alkyl group or an optionally substituted carbocyclic and heterocyclic group comprising five-, six- or ten-membered ring systems and the like.

$S_1$ is preferably a straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO$_3$R'—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof.

More preferably, $S_1$ is straight-chain or branched C1-C8 alkyl, which is unsubstituted or substituted by at least one CN, Hal, or $NO_2$, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof.

As indicated hereinabove, $S_1$ may specifically include amino acids, which as used herein are compounds with both an amino group (e.g., $NH_2$ or $NH_3^+$) and a carboxylic acid group (e.g., COOH or COO$^-$). In a specific embodiment, the amino acid may be an α-amino acid, a β-amino acid, a D-amino acid or an L-amino acid. The amino acid may be a naturally occurring amino acid (e.g., alanine, valine, leucine, isoleucine, proline, phenylalanine, tryptophan, methionine, glycine, serine, threonine, cysteine, tyrosine, asparagine, aspartic acid, glutamic acid, lysine, arginine, or histidine, etc.) or it may be a derivative thereof.

Examples of derivatives include optionally substituted amino acids, e.g. having one or more substituents selected from CN, Hal, and/or $NO_2$. The amino acid may also include any other non-naturally occurring amino acids, such as e.g. norleucine, norvaline, L- or D-naphthalanine, ornithine, homoarginine and others well known in the peptide art (see for for example in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference). Amino acids and amino acid analogs/derivatives can be purchased commercially (Sigma Chemical Co.; Advanced Chemtech) or synthesized using methods known in the art. In another specific embodiment, the amino acid may also be part of a polyamino acid (also termed polypeptide), wherein a plurality of same or different amino acids as defined hereinabove are covalently linked, i.e. linked through conventional peptide or other bonds. Preferred amino acids include for example glutamic acid, aspartic acid, glutamine, aspartine, lysine, arginine, cystein, and derivatives thereof and preferred polyamino acids include homopolymers the respective homopolymers thereof (i.e. polyglutamic acid, polyaspartic acid, etc). Most preferred are optionally substituted aspartic and glutamic acid.

Groups $X_1$ to $X_5$, $R_1$ to $R_5$, p and q are defining the nature of group P in more detailed manner. A person skilled in the art would though know the range of these groups within the pteroic and/or folic acid skeleton.

Thus, $X_1$ to $X_5$ as used herein are independently of each other C or N.

In a preferred embodiment, $R_1$ and $R_2$ are independently of each other represent H, alkyl, —OR', —NHR', more preferably —OR',—NHR'.

In a preferred embodiment, $R_3$ is H, C1-C12 alkyl or C1-C12 alkanoyl.

In another preferred embodiment, $R_4$ is H, nitroso, C1-C12 alkoxy, or C1-C12 alkanoyl.

In another preferred embodiment, $R_5$ is H, CN, Hal, $NO_2$, C1-C12 alkyl, C1-C12 alkoxy, C1-C12 alkanoyl, C2-C12 alkenyl, C2-C12 alkynyl, (C1-C12 alkoxy)carbonyl, (C1-C12 alkylamino)carbonyl. More preferably, $R_5$ is H, C1-C12 alkyl, C1-C12 alkoxy, C1-C12 alkanoyl, (C1-C12 alkoxy) carbonyl, and (C1-C12 alkylamino)carbonyl.

It is understood, that $(H)_q$ represents all H substituents on the indicated ring (i.e. on X3, C6, C7 and X4), thus q may have a value of 1 to 7. For example q=7 stands for a fully saturated 5,8-dideaza analog (X3=X4=C) and q=1 for a fully unsaturated analog with X3=X4=N.

It is also understood, that p depends on the nature of X and the aromaticity of the ring and thus may be 0, 1 or 2.

It is further understood, that the abbreviations "N" and "C" are representative for all possible degrees of saturation, i.e. N includes —NH— and —N= linkages and C includes —$CH_2$— and —CH= linkages.

In another preferred embodiment, the present invention is directed towards a method of synthesis in accordance with scheme 1, wherein the glutamate moiety of a folic acid or derivative thereof is directly radiolabeled with $^{18}$F and the obtained compound has thus the formula V

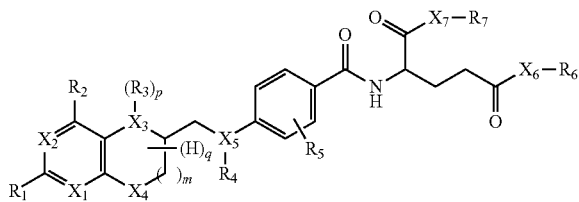

V wherein $X_6$, $X_7$ are independently of each other C, N or O, $R_6$, $R_7$ are independently of each other H, straight chain or branched $C_1$-$C_{12}$ alkyl, which is unsubstituted or substituted by at least one CN, Hal, or $NO_2$ or a group —$S_2$—$^{18}F$, wherein $S_2$ is straight chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3R'$—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof, with the proviso that at least one of $R_6$ and $R_7$ is a group —$S_2$—$^{18}F$, and $X_1$ to $X_5$, $R_1$ to $R_5$, m, p and q, and preferred embodiments thereof are as defined hereinabove.

Thus more specifically, the obtained compound of formula V may be represented by compounds having the formulae VI or VIa,

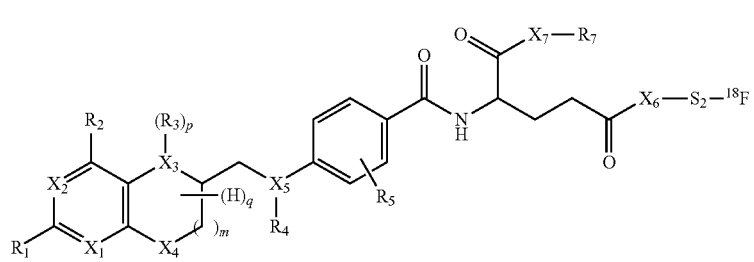

VI

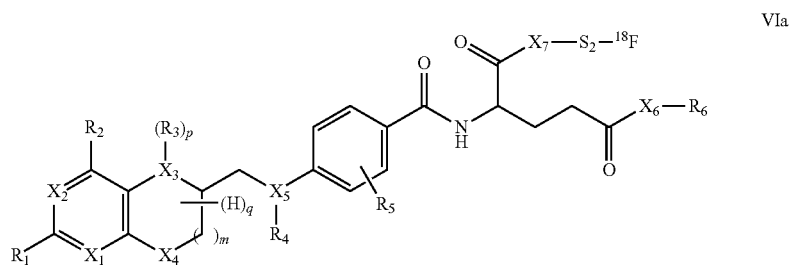

VIa wherein $X_1$ to $X_5$, $R_1$ to $R_7$, m, p and q, and preferred embodiments thereof are as defined hereinabove.

Thus, the present invention contemplates in a specific embodiment a method of synthesis of an $^{18}F$-labeled compound of general formulae VI or VIa in accordance with scheme 1,

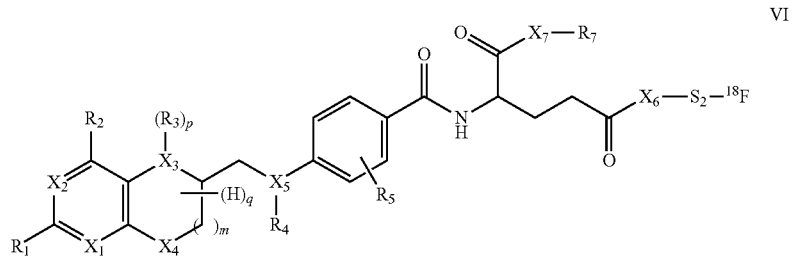

VI

-continued

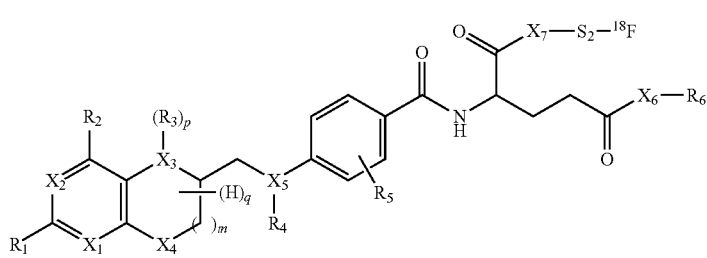

VIa

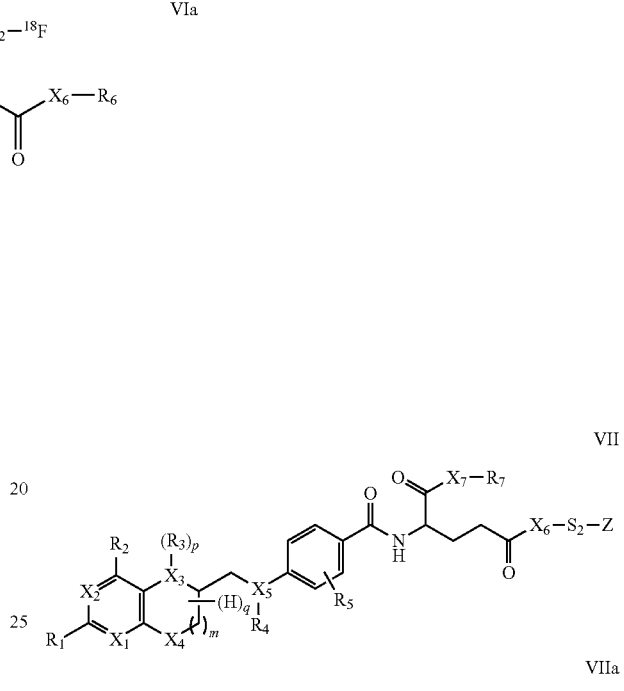

VII

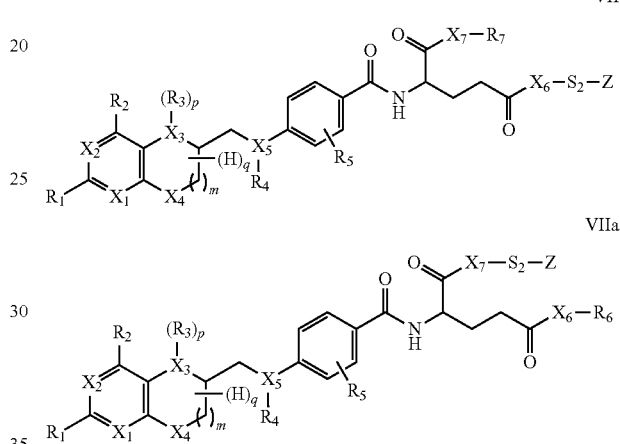

VIIa wherein $X_1$ to $X_5$ are independently of each other C or N, $X_6$, $X_7$ are independently of each other C, O or N, $R_1$, $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$ is H, CN, Hal, $NO_2$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, $R_6$, $R_7$ are independently of each other H or straight chain or branched $C_1$-$C_{12}$ alkyl, which is unsubstituted or substituted by at least one CN, Hal, or $NO_2$, $S_2$ is straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, C≡C—, —S—, —$SO_3$R'—, —PR'—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof, m is 0 or 1, p is 0, 1 or 2, and q has a value of 1 to 7, comprising the steps of (a) providing a precursor of formulae VII or VIIa, wherein Z is a leaving group, and $X_1$ to $X_7$, $R_1$ to $R_7$, $S_2$, m, p, and q are defined as hereinabove, and (b) subjecting said precursor to direct radiolabeling with $^{18}F$.

$S_2$ is preferably straight chain or branched C1-C8 alkyl, which is unsubstituted or substituted by at least one CN, Hal, or $NO_2$, or a five- or six-membered aromatic ring, which is unsubstituted or substituted with CN, Hal, $NO_2$, COR', or COOR', wherein R' represents H or C1-C6 alkyl, or a combination thereof, more preferably straight-chain or branched C1-C6 alkyl, which is unsubstituted or substituted by at least one CN, Hal, or $NO_2$.

A further specific embodiment of the compounds of the invention includes for example compounds wherein $X_1$ to $X_5$ are N, $R_1$ is $NY_1Y_2$, $R_2$ is O, $R_4$ is $Y_3$, p is 0 and q is 1.

Thus, in a further specific embodiment the present invention is directed to a compounds of formulae VIII or VIIIa,

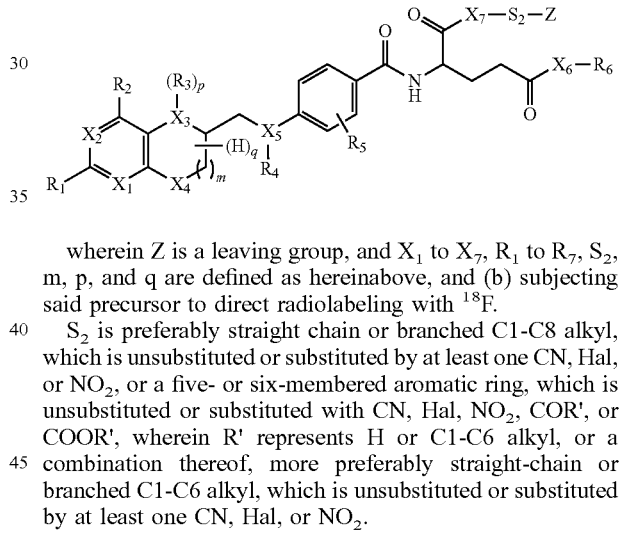

VIII

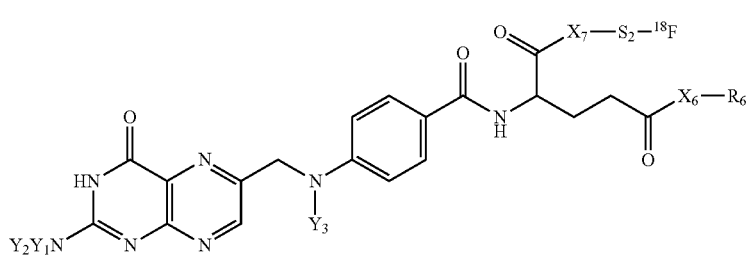

VIIIa $X_6$, $X_7$ are independently of each other C, N or O, $Y_1$, $Y_2$ are independently of each other selected from H, formyl, straight chain or branched $C_1$-$C_{12}$ alkyl, which is unsubstituted or substituted by at least one CN, Hal, or $NO_2$, $Y_3$ is selected from H, formyl, nitroso, straight chain or branched $C_1$-$C_{12}$ alkyl, which is unsubstituted or substituted by at least one CN, Hal, or $NO_2$, $R_6$, $R_7$ are independently of each other H or straight chain or branched $C_1$-$C_{12}$ alkyl, which is unsubstituted or substituted by at least one CN, Hal, or $NO_2$, and $S_2$ is straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR=—, or a five- or six-membered aromatic ring having 0, 1 or 2 heteroatoms, which is unsubstituted or substituted with CN, Hal, $NO_2$, COR', or COOR', wherein R' represents H or C1-C6 alkyl, or a combination thereof.

The term "alkyl", when used singly or in combination, refers to straight chain or branched alkyl groups containing 1 to 12 carbon atoms, such as methyl, ethyl, propyl, isopropyl, butyl, secbutyl, isobutyl, t-butyl, pentyl isopentyl, neopentyl, hexyl and the like. The preferred alkyl groups contain 1 to 8, more preferably 1 to 4 carbon atoms.

As used herein, the term "alkenyl", singly or in combination with other groups, refers to straight chain or branched alkyl groups containing 2 to 12 carbon atoms, such as methylene, ethylene, propylene, isopropylene, butylene, t-butylene, secbutylene, isobutylene, amylene, isoamylene, pentylene, isopentylene, hexylene and the like. The preferred alkenyl groups contain 2 to 6 carbon atoms.

The term "alkynyl" as used herein refers to a linear or branched chain of carbon atoms with one or more carbon-carbon triple bonds. The preferred alkynyl groups contain 2 to 12, more preferably 2 to 6 carbon atoms.

The term "alkoxy" as used herein refers to alkyl, as defined above, substituted with oxygen, such as methoxy, ethoxy, propoxy, isopropoxy, butoxy, tert-butoxy and the like.

The term "alkanoyl" as used herein refers to formyl, or alkyl, as defined above, terminally-substituted with a carbonyl such as acetyl, propanoyl, butanoyl, pentanoyl and the like.

The term "alkylamino" as used herein refers to alkyl, as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halo" as used herein refers to any Group 7 element and includes fluoro, chloro, bromo, iodo, and astatine(o).

In a further aspect the present invention is directed towards compounds obtained by the methods of the invention, such as compounds of formulae I to VIII.

In yet a further aspect the present invention provides uses of the new folate radiopharmaceuticals obtained by the method of the invention for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by PET imaging.

In a further aspect the present invention provides uses of folate radiopharmaceuticals of the present invention for convenient and effective administration to a subject in need for diagnostic imaging or monitoring of cancer therapy and therapy of inflammatory and autoimmune diseases.

In another aspect the present invention provides a method for simultaneous diagnosis and therapy, comprising the steps of administering to a subject in need thereof at least one folate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect. The imaging procedure in the PET scanner takes place from within minutes to 2-4 hours after administration of the radiotracer. The schedule depends on the imaging target and kinetics of the radiotracer as well as the desired information.

The preferred route of administration of the folate radiopharmaceuticals of the present invention is by intraveneous injection.

The suitable forms for injection include sterile aqueous solutions or dispersions of the above mentioned folate radiopharmaceuticals of the present invention. Typically the radiopharmaceutical will be formulated in physiological buffer solutions.

The folate radiopharmaceuticals undergo sterilization by any art recognized technique, including but not limited to, addition of antibacterial of antifungal agents, for example, paraben, chlorobutanol, phenol, sorbic acid, thimerosal, and the like. Preferably they undergo a sterile filtration before administration eliminating the need of additional sterilisation agents.

For a solution to be injected a preferred unit dosage is from about 0.01 mL to about 10 mL. After intravenous administration, imaging of the organ or tumor in vivo can take place, if desired, from within minutes to 2 to 4 hours after the radiolabeled reagent has been administered to a subject to allow a sufficient amount of the administered dose to accumulate in the targeted area of choice.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumor cells, epithelial cells, kidneys, gastrointestinal or the hepatobiliary system, and others. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the complexes or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

Infrared spectra were recorded on a Jasco FT/IR-6200 ATR-IR. Nuclear magnetic resonance spectra were recorded with a Bruker 400 MHz or 500 MHz spectrometer with the corresponding solvent signals as an internal standard. Chemical shifts are reported in parts per million (ppm) relative to tetramethylsilane (0.00 ppm). Values of the coupling constant, J, are given in Hertz (Hz); the following abbreviations are used in the experimental section for the description of $^1$H-NMR spectra: singlet (s), doublet (d), triplet (t), multiplet (m), doublet of doublets (dd). The chemical shifts of complex multiplets are given as the range of their occurrence. Low resolution mass spectra (LR-MS) were recorded with a Micromass Quattro micro™ API LC-ESI.

Water sensitive reactions were run under argon in flame-dried glass ware. Reactions were monitored by thin layer chromatography (TLC, performed on EM Science 0.25 mm thick, precoated silica gel 60 F-254 glass supported plates) or HPLC. HPLC was performed on a Merck-Hitachi L-7000 system equipped with an L-7400 tunable absorption detector. Analytical HPLC was performed with an XBridge® column (C18, 5 μm, 4.6×150 mm, Waters) using the following solvent system (1 mL/min): 0.1% TFA$_{aq}$ (solvent A), acetonitril (solvent B), 1 mL/min; 0-1 min, 95% A; 1-15 min, 95→5% A; 15-20 min, 5% A; 20→22 min, 5→95% A; 22→25 min, 95%

A. Semi-prep HPLC was performed with XBridge® semiprep column (C18, 5 μm, 10×150 mm, Waters), 3 mL/min, isochratic NH$_4$HCO$_3$ (10 mM, 88%)/CH$_3$CN (12%). All chemicals were used as supplied unlike stated otherwise.

Example 1

Synthesis of γ-2-fluoroethyl-folic Acid (a) Synthesis of γ-Glu(fluoroethyl) methyl ester In a flame dried flask was added BOC-Glu-OMe (556 mg, 2.13 mmol), dry DMF (10 ml) and Et3N (0.9 ml, 1.9 e.q.). The reaction mixture was cooled to 0° C., and HBTU (808 mg, 1 e.q.) was added and the reaction mixture was stirred for 10 mins. A solution of 2-fluoroethylamine (212 ml, 1 e.q.) in dry DMF (10 ml) and Et3N (0.9 ml, 1.9 e.q.) was added dropwise to the reaction mixture at 0° C. The reaction was stirred for 2 h, allowed to warm to r.t. and stirred overnight. Water (10 ml) was added to the reaction mixture, and it was extracted with EtOAc. The combined organic layers were washed with brine, dried with MgSO$_4$, and concentrated in vacuo to give a pale yellow oil. $^1$H-NMR (300 MHz, DMSO-d$_6$) [ppm]: 7.78 (bs, NH); 6.60 (bs, NH); 4.77 (bs, OH); 4.62 (t, CH); 3.47 (m, CH$_3$); 3.37 (t, CH$_2$); 3.11 (t, CH$_2$); 2.89 (t, CH$_2$); 2.73 (t, CH$_2$); 1.39 (s, CH$_3$)

(b) Synthesis of γ-2-fluoroethyl-folic acid

γ-Glu(fluoroethyl)methyl ester (450 mg, 1.48 mmol) was dissolved in excess TFA/CH$_2$Cl$_2$ (1:1) until complete BOC deprotection occurred as monitored by TLC/HPLC. Excess TFA/CH$_2$Cl$_2$ was removed under vacuo to give the TFA salt of Glu(hydroxyethyl)methyl ester as pale yellow oil, which was directly used in the coupling reaction with N2-N,N-dimethylaminomethylene-10-formyl-pteroic acid according to the procedures outlined in EP A 07 105 987 and EP A 07 105 984.

Example 2

Synthesis of γ-(2-(p-toluenesulfonyl)ethyl)_folic Acid Amide (a) Synthesis of BOC-Glu(hydroxyethyl) methyl ester In a flame dried flask was added BOC-Glu-OMe (556 mg, 2.13 mmol), dry DMF (10 ml) and Et3N (0.9 ml, 1.9 e.q.). The reaction mixture was cooled to 0° C., and HBTU (808 mg, 1 e.q.) was added and the reaction mixture was stirred for 10 mins. A solution of amino alcohol (0.13 ml, 1 e.q.) in dry DMF (10 ml) and Et3N (0.9 ml, 1.9 e.q.) was added dropwise to the reaction mixture at 0° C. The reaction was stirred for 2 h, allowed to warm to r.t. and stirred overnight. Water (10 ml) was added to the reaction mixture, and it was extracted with EtOAc. The combined organic layers were washed with brine, dried with MgSO$_4$, and concentrated in vacuo to give a pale yellow oil. $^1$H-NMR (300 MHz, DMSO-d$_6$) [ppm]: 9.40 (bs, NH); 7.72 (bs, NH); 4.52 (t, CH); 3.54 (m, CH$_3$); 3.44 (t, CH$_2$); 3.14 (t, CH$_2$); 2.56 (t, CH$_2$); 2.20 (t, CH$_2$); 1.24 (s, CH$_3$).

(b) Synthesis of γ-(2-(p-toluenesulfonyl)ethyl) folic acid amide

BOC-Glu(hydroxyethyl)methyl ester (450 mg, 1.48 mmol) was dissolved in excess TFA/CH$_2$Cl$_2$ (1:1) until complete BOC deprotection occurred as monitored by TLC/HPLC. Excess TFA/CH$_2$Cl$_2$ was removed under vacuo to give the TFA salt of Glu(hydroxyethyl)methyl ester as pale yellow oil, which was directly used in the coupling reaction with N2-N,N-dimethylaminomethylene-10-formyl-pteroic acid according to the procedures outlined in EP A 07 105 987 and EP A 07 105 984. γ-(2-hydroxyethyl)folic acid amide (26 μmol) was dissolved in dichloromethane (10 ml) and cooled to 0° C. Et$_3$N (10 μl, 1.5 eq.) and TsCl (7 mg, 1.4 eq.) were added and the reaction mixture was stirred for 2 h at 0° C. Then the mixture was allowed to warm to room temperature and stirred overnight.

The reaction mixture was poured into water (15 ml), layers were separated. The aqueous phase was extracted with dichloromethane and combined organic phases were dried over MgSO$_4$. The solvents were removed under vacuo. The product was purified by column chromatography using silica gel and an eluent system of pentane and ethyl acetate to give a yellow oil.

This compound serves then as precursor for a direct aliphatic nucleophilic $^{18}$F-labelling according to literature procedures (Coenen, H. H. PET Chemistry—The Driving Force in Molecular Imaging, Schubiger, P. A.; Lehmann, L.; Friebe, M., Eds.; Springer: Berlin, 2007, pp. 15-50).

The invention claimed is:

1. A method of direct radiolabeling of the glutamate moiety of a folate compound with $^{18}$F comprising:

reacting a compound of formulae VII or VIIa with $^{18}$F,

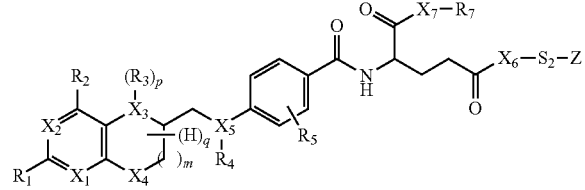

VII

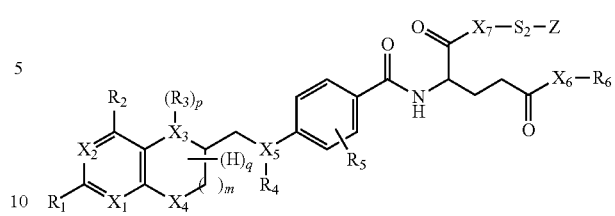

VIIa wherein
$X_1$ to $X_5$ are N,
$X_6$, $X_7$ are independently of each other O or NH,
$R_1$, $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl,
R' is H or C1-C6 alkyl,
$R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl,
$R_5$ is H, CN, Hal, NO$_2$, C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl,
$R_6$, $R_7$ are independently of each other H or straight chain or branched C1-C12 alkyl, which is unsubstituted or substituted by at least one CN, Hal, or NO$_2$,
$S_2$ is straight chain or branched C1-C6 alkyl, which is unsubstituted or substituted by at least one CN, Hal, or NO$_2$,
m is 1,
p is 0, 1 or 2,
q has a value of 1 to 7,
Z is a leaving group, and
wherein $^{18}$F is activated by phase transfer catalyst in combination with potassium carbonate or oxalate,
to obtain a $^{18}$F-labeled compound of formulae VI or VIa,

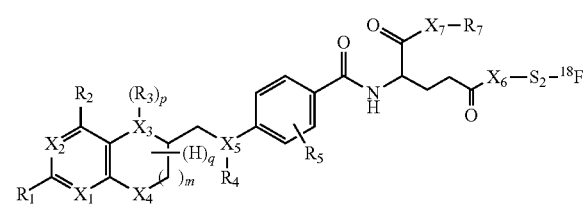

VI

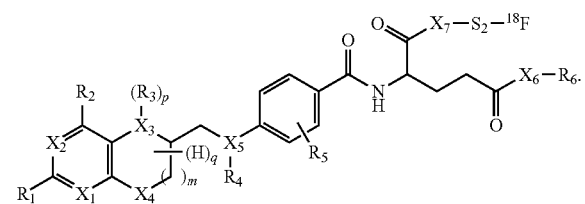

VIa

2. A method according to claim 1, wherein $^{18}$F is activated using 4,7,13,16,21,24-hexaoxa-1,10-diazabicyclo[8,8,8]hexacosane as the phase transfer catalyst in a polar solvent selected from acetonitrile, acetone, 1,4-dioxane, tetrahydrofuran, N-methylpyrrolidinone, di-methoxyethane, dimethylacetamide, N,N-dimethylformamide, dimethylsulfoxide, hexa-methylphosphoramide and mixtures thereof.

3. A method according to claim 1, wherein Z is selected from Hal, NO$_2$, diazonium salts, sulfonate esters, iodonium salts, dialkyl/-aryl silanes, and silanols.

4. A method according to claim 1, wherein the obtained $^{18}$F-labeled compound is of formulae VIII or VIIIa, 5. A method according to claim 1, wherein the phase transfer catalyst is tetrabutylamonium carbonate or an aminopolyether.

6. A method according to claim 1, wherein the phase transfer catalyst is 4,7,13,16,21,24-Hexaoxa-1,10-diazabicyclo[8.8.8]hexacosane.

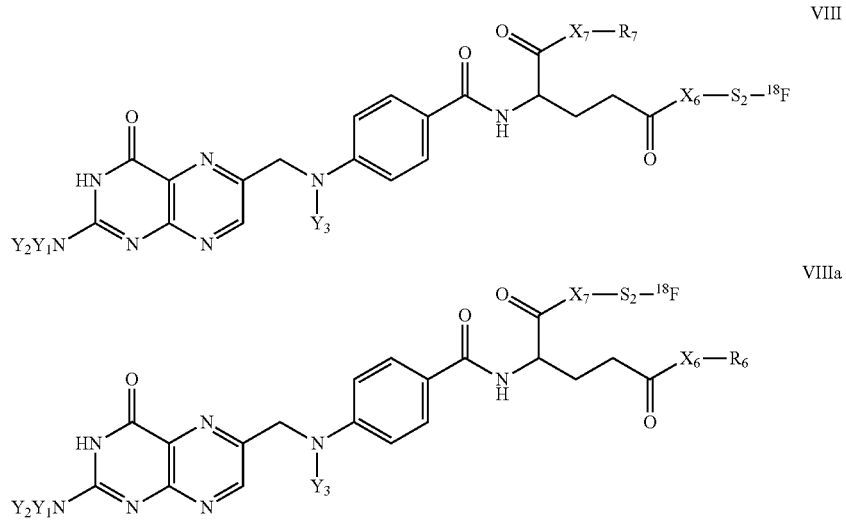

wherein,
- $X_6$, $X_7$ are independently of each other NH or O,
- $Y_1$, $Y_2$ are independently of each other H, straight chain or branched C1-C4 alkyl,
- $Y_3$ is H, formyl, nitroso, straight chain or branched C1-C12 alkyl,
- $R_6$, $R_7$ are independently of each other H or straight chain or branched C1-C12 alkyl, which is unsubstituted or substituted by at least one CN, Hal, or NO$_2$, and
- $S_2$ is straight chain or branched C1-C6 alkyl, which is unsubstituted or substituted by at least one CN, Hal, or NO$_2$.

7. A method according to claim 3, wherein Z is mesylate, tosylate, pentafluorobenzoate, or triflate.

8. A method according to claim 2, wherein Z is selected from Hal, NO$_2$, diazonium salts, sulfonate esters, iodonium salts, dialkyl/-aryl silanes, and silanols.

9. A method according to claim 8, wherein Z is mesylate, tosylate, pentafluorobenzoate, or triflate.

10. A method according to claim 2, wherein the obtained $^{18}$F-labeled compound is of formulae VIII or VIIIa,

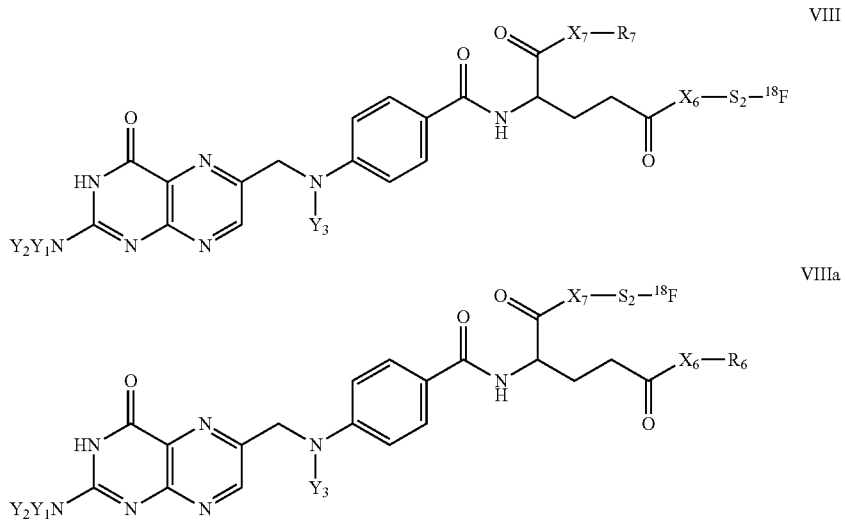

wherein, $X_6$, $X_7$ are independently of each other NH or O, $Y_1$, $Y_2$ are independently of each other H, straight chain or branched C1-C4 alkyl, $Y_3$ is H, formyl, nitroso, straight chain or branched C1-C12 alkyl, $R_6$, $R_7$ are independently of each other H or straight chain or branched C1-C12 alkyl, which is unsubstituted or substituted by at least one CN, Hal, or $NO_2$, and $S_2$ is straight chain or branched C1-C6 alkyl, which is unsubstituted or substituted by at least one CN, Hal, or $NO_2$.

11. A method according to claim 3, wherein the obtained $^{18}F$-labeled compound is of formulae VIII or VIIIa,

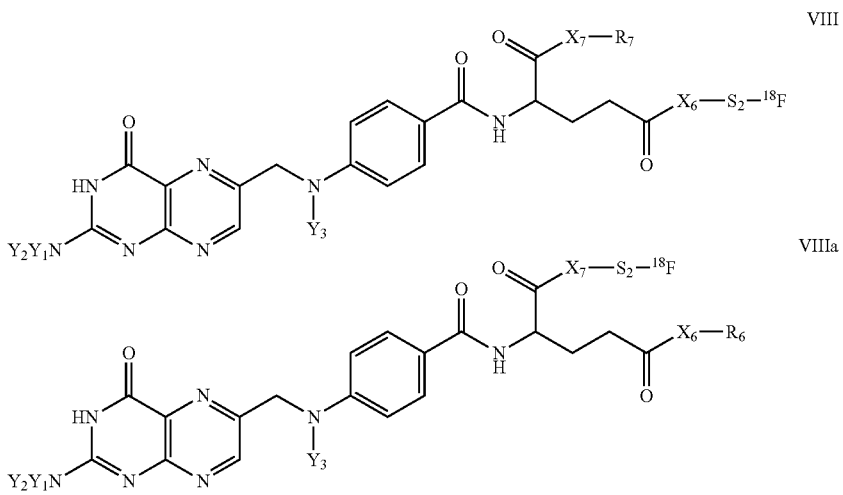

wherein, $X_6$, $X_7$ are independently of each other NH or O, $Y_1$, $Y_2$ are independently of each other H, straight chain or branched C1-C4 alkyl, $Y_3$ is H, formyl, nitroso, straight chain or branched C1-C12 alkyl, $R_6$, $R_7$ are independently of each other H or straight chain or branched C1-C12 alkyl, which is unsubstituted or substituted by at least one CN, Hal, or $NO_2$, and $S_2$ is straight chain or branched C1-C6 alkyl, which is unsubstituted or substituted by at least one CN, Hal, or $NO_2$.

12. A method according to claim 8, wherein the obtained $^{18}F$-labeled compound is of formulae VIII or VIIIa,

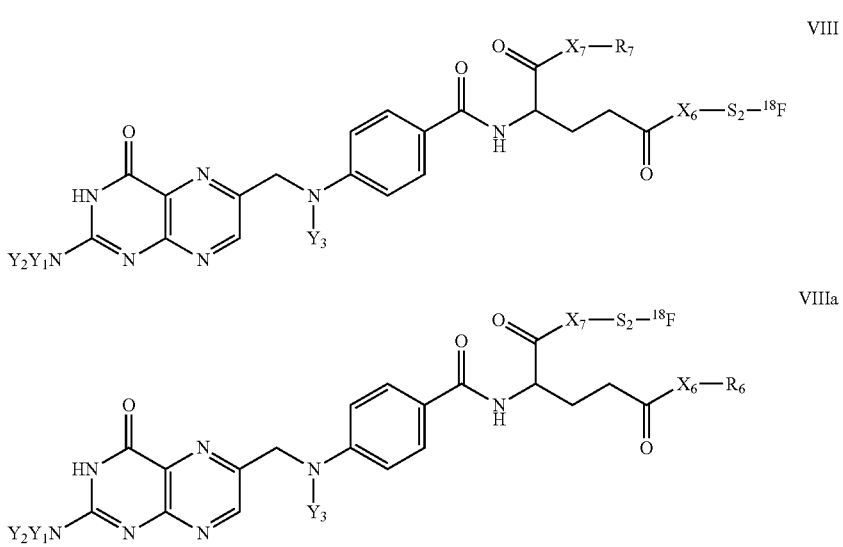

wherein, $X_6$, $X_7$ are independently of each other NH or O, $Y_1$, $Y_2$ are independently of each other H, straight chain or branched C1-C4 alkyl, $Y_3$ is H, formyl, nitroso, straight chain or branched C1-C12 alkyl, $R_6$, $R_7$ are independently of each other H or straight chain or branched C1-C12 alkyl, which is unsubstituted or substituted by at least one CN, Hal, or $NO_2$, and $S_2$ is straight chain or branched C1-C6 alkyl, which is unsubstituted or substituted by at least one CN, Hal, or $NO_2$.

13. A method according to claim 1, wherein $X_6$ and $X_7$ are each O.

14. A method according to claim 1, wherein $X_6$ and $X_7$ are each NH.

\* \* \* \* \*